(12) United States Patent
Liu

(10) Patent No.: US 11,497,408 B2
(45) Date of Patent: Nov. 15, 2022

(54) IMAGE INFORMATION GENERATION METHOD, PULSE WAVE MEASUREMENT SYSTEM AND ELECTRONIC DEVICE

(71) Applicant: BOE TECHNOLOGY GROUP CO., LTD., Beijing (CN)

(72) Inventor: Cheng Liu, Beijing (CN)

(73) Assignee: Beijing BOE Technology Development Co., Ltd., Beijing (CN)

(*) Notice: Subject to any disclaimer, the term of this patent is extended or adjusted under 35 U.S.C. 154(b) by 660 days.

(21) Appl. No.: 16/485,763

(22) PCT Filed: Jan. 15, 2019

(86) PCT No.: PCT/CN2019/071772
§ 371 (c)(1),
(2) Date: Aug. 13, 2019

(87) PCT Pub. No.: WO2020/001006
PCT Pub. Date: Jan. 2, 2020

(65) Prior Publication Data
US 2020/0383591 A1 Dec. 10, 2020

(30) Foreign Application Priority Data
Jun. 26, 2018 (CN) .......................... 201810671558.0

(51) Int. Cl.
*G06T 7/246* (2017.01)
*A61B 5/00* (2006.01)
(Continued)

(52) U.S. Cl.
CPC .......... *A61B 5/02433* (2013.01); *A61B 5/489* (2013.01); *G06T 5/003* (2013.01);
(Continued)

(58) Field of Classification Search
CPC ... G06T 3/0068; G06T 7/0012; G06T 7/0014; G06T 7/0016; G06T 7/30; G06T 7/33;
(Continued)

(56) References Cited

U.S. PATENT DOCUMENTS

| 9,095,285 B2 | 8/2015 | Ryabov et al. | |
| 2013/0034287 A1* | 2/2013 | Itagaki et al. | G01R 33/5635 |
| | | | 382/131 |

(Continued)

FOREIGN PATENT DOCUMENTS

| CN | 102283675 A | 12/2011 |
| CN | 103491328 A | 1/2014 |

(Continued)

OTHER PUBLICATIONS

First Office Action for CN Appl. No. 201810671558.0, dated Apr. 20, 2020.
(Continued)

*Primary Examiner* — Andrew W Johns
(74) *Attorney, Agent, or Firm* — The Webb Law Firm

(57) ABSTRACT

The present disclosure relates to an image information generation method, a pulse wave measurement system and an electronic device. The method comprises: with respect to a target part, acquiring a first infrared image sequence, each infrared image in the first infrared image sequence including at least a vein pattern; by registering the vein pattern in each infrared image in the first infrared image sequence, correcting each infrared image in the first infrared image sequence, thereby obtaining the corrected first infrared image sequence; removing at least the vein regions from respective infrared images in the corrected first infrared image sequence, to obtain image information of remaining regions as image information for pulse wave measurement.

20 Claims, 10 Drawing Sheets

(51) Int. Cl.
*A61B 5/024* (2006.01)
*G06T 5/00* (2006.01)
*G06V 40/10* (2022.01)
*G06V 40/14* (2022.01)

(52) U.S. Cl.
CPC .............. *G06T 7/248* (2017.01); *G06V 40/10* (2022.01); *A61B 2576/00* (2013.01); *G06T 2207/10016* (2013.01); *G06T 2207/10048* (2013.01); *G06T 2207/30101* (2013.01); *G06V 40/14* (2022.01)

(58) Field of Classification Search
CPC .............. G06T 7/38; G06T 2207/10048; G06T 2207/30101; G06V 40/14; A61B 5/02416; A61B 5/02433; A61B 5/0261; A61B 5/489
See application file for complete search history.

(56) References Cited

U.S. PATENT DOCUMENTS

| | | | |
|---|---|---|---|
| 2015/0002647 A1* | 1/2015 | Qian | A61B 5/0077 348/77 |
| 2016/0117563 A1 | 4/2016 | Shin et al. | |
| 2017/0262985 A1* | 9/2017 | Finn et al. | G06T 7/149 |
| 2018/0197291 A1* | 7/2018 | Jiang et al. | A61B 5/0064 |
| 2020/0074635 A1* | 3/2020 | Satoh et al. | G01R 33/443 |

FOREIGN PATENT DOCUMENTS

| | | |
|---|---|---|
| CN | 103908236 A | 7/2014 |
| CN | 104622439 A | 5/2015 |
| CN | 105188522 A | 12/2015 |
| CN | 107194367 A | 9/2017 |
| CN | 107837076 A | 3/2018 |
| CN | 107967466 A | 4/2018 |
| CN | 108742549 A | 11/2018 |
| TW | I617281 B | 3/2018 |
| WO | WO-2014/017697 A1 | 1/2014 |

OTHER PUBLICATIONS

Humphreys et al., "Noncontact simultaneous dual wavelength photoplethysmography: A further step toward noncontact pulse oximetry", Review of Scientific Instruments, 78, 044304, 2007, 7 pages.

Kong, Lingqin, "Research on Key Techniques of the Noncontact Detection of Physiological Signals", Beijing Institute of Technology, School of Optpelectronics, Jun. 2014, 403 pages with English language translation.

* cited by examiner

WITH RESPECT TO A TARGET PART, ACQUIRING A FIRST INFRARED IMAGE SEQUENCE, EACH INFRARED IMAGE IN THE FIRST INFRARED IMAGE SEQUENCE INCLUDING AT LEAST A VEIN PATTERN;
101

BY REGISTERING THE VEIN PATTERN IN EACH INFRARED IMAGE IN THE FIRST INFRARED IMAGE SEQUENCE, CORRECTING EACH INFRARED IMAGE IN THE FIRST INFRARED IMAGE SEQUENCE, THEREBY OBTAINING THE CORRECTED FIRST INFRARED IMAGE SEQUENCE;
102

REMOVING AT LEAST THE VEIN REGIONS FROM RESPECTIVE INFRARED IMAGES IN THE CORRECTED FIRST INFRARED IMAGE SEQUENCE, TO OBTAIN IMAGE INFORMATION OF REMAINING REGIONS AS IMAGE INFORMATION FOR PULSE WAVE MEASUREMENT.
103

FIG. 1

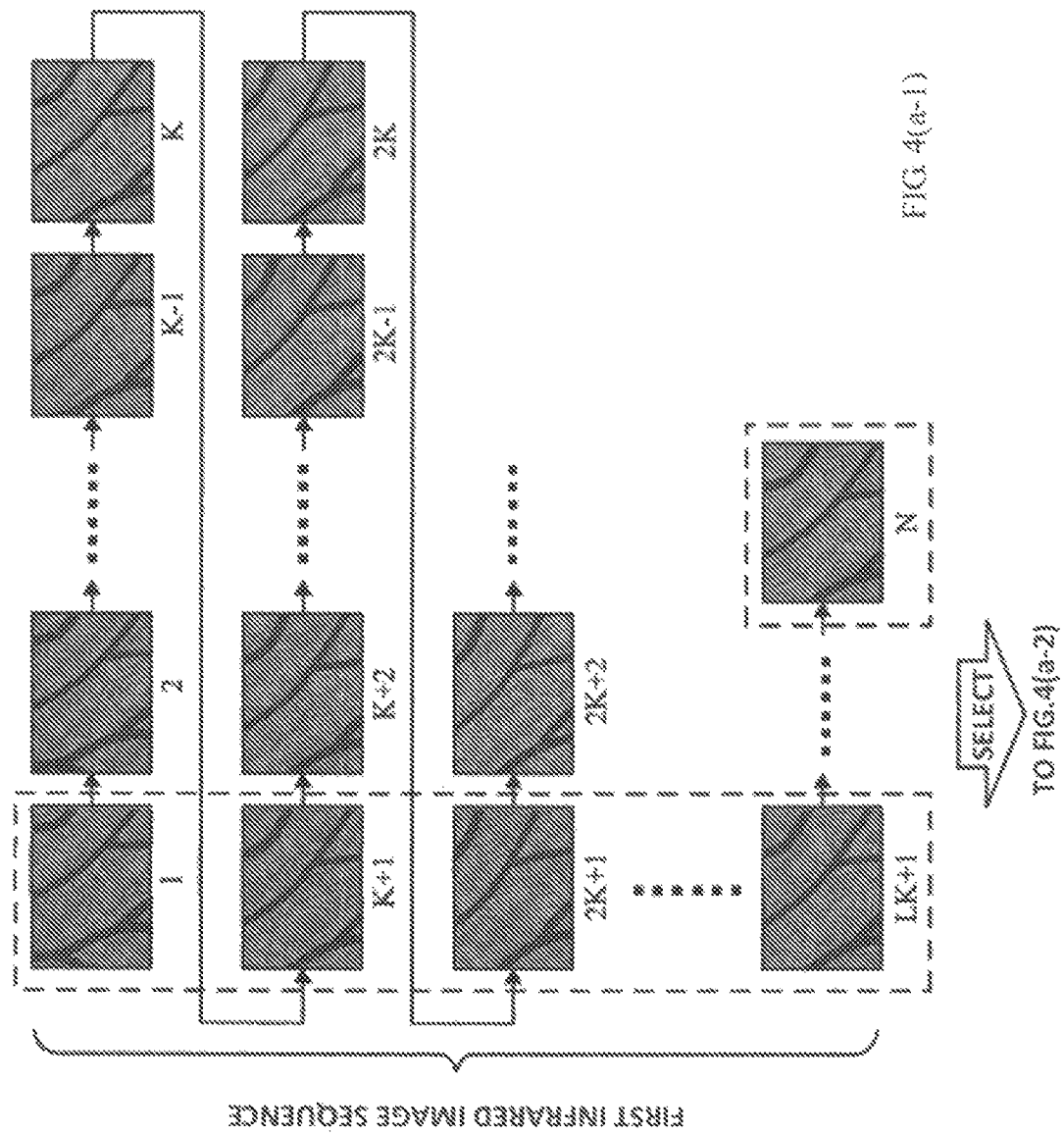

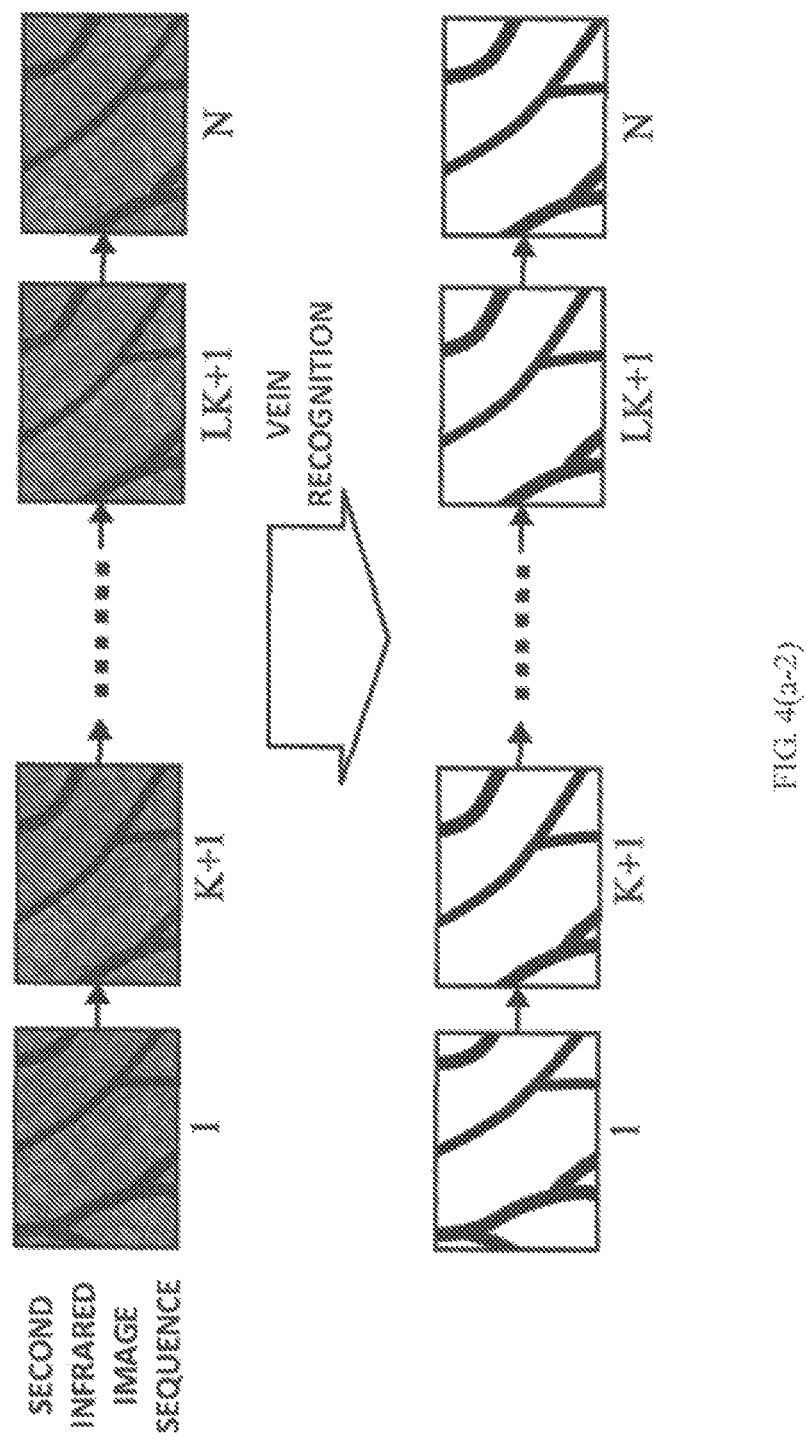
FIG. 4(a-2)

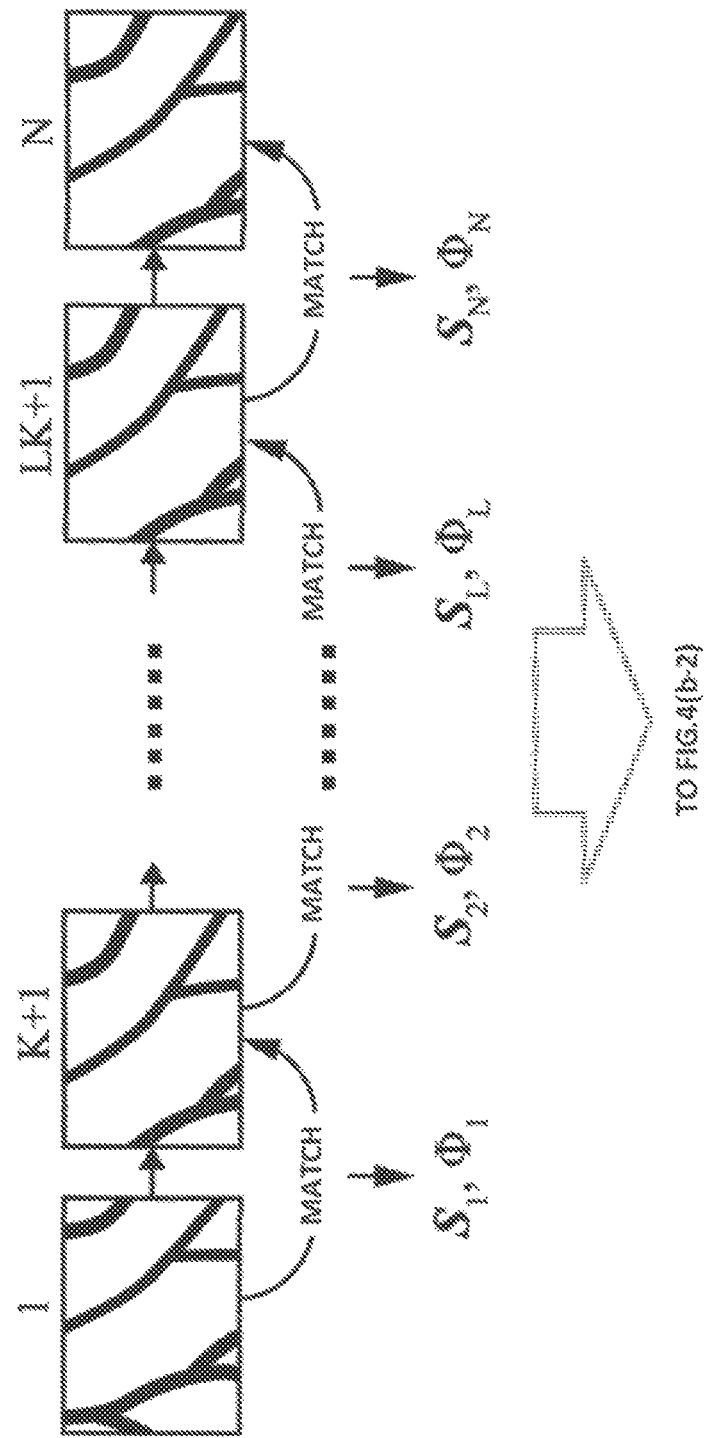
FIG. 4(b-1)

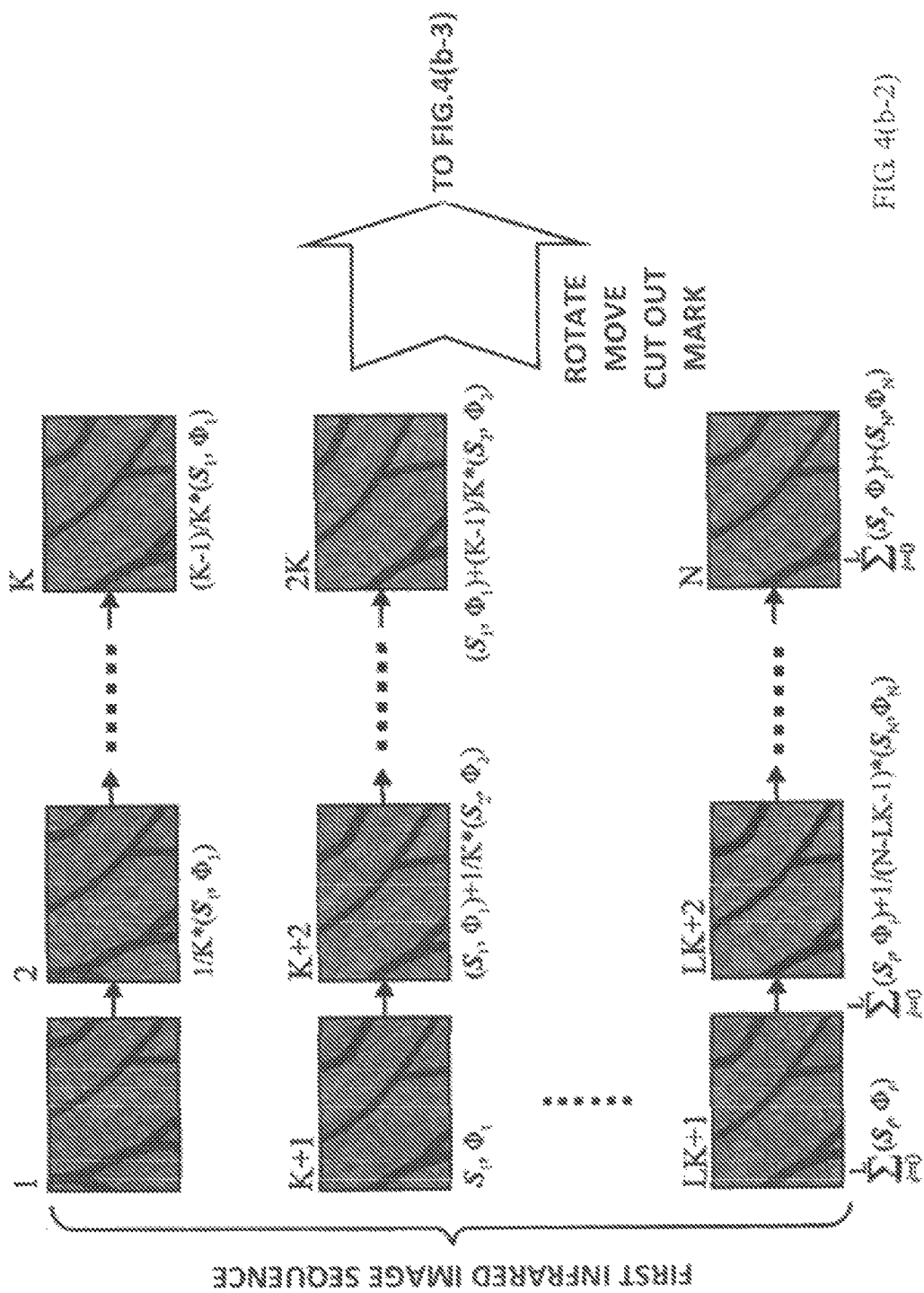
FIG. 4(b-2)

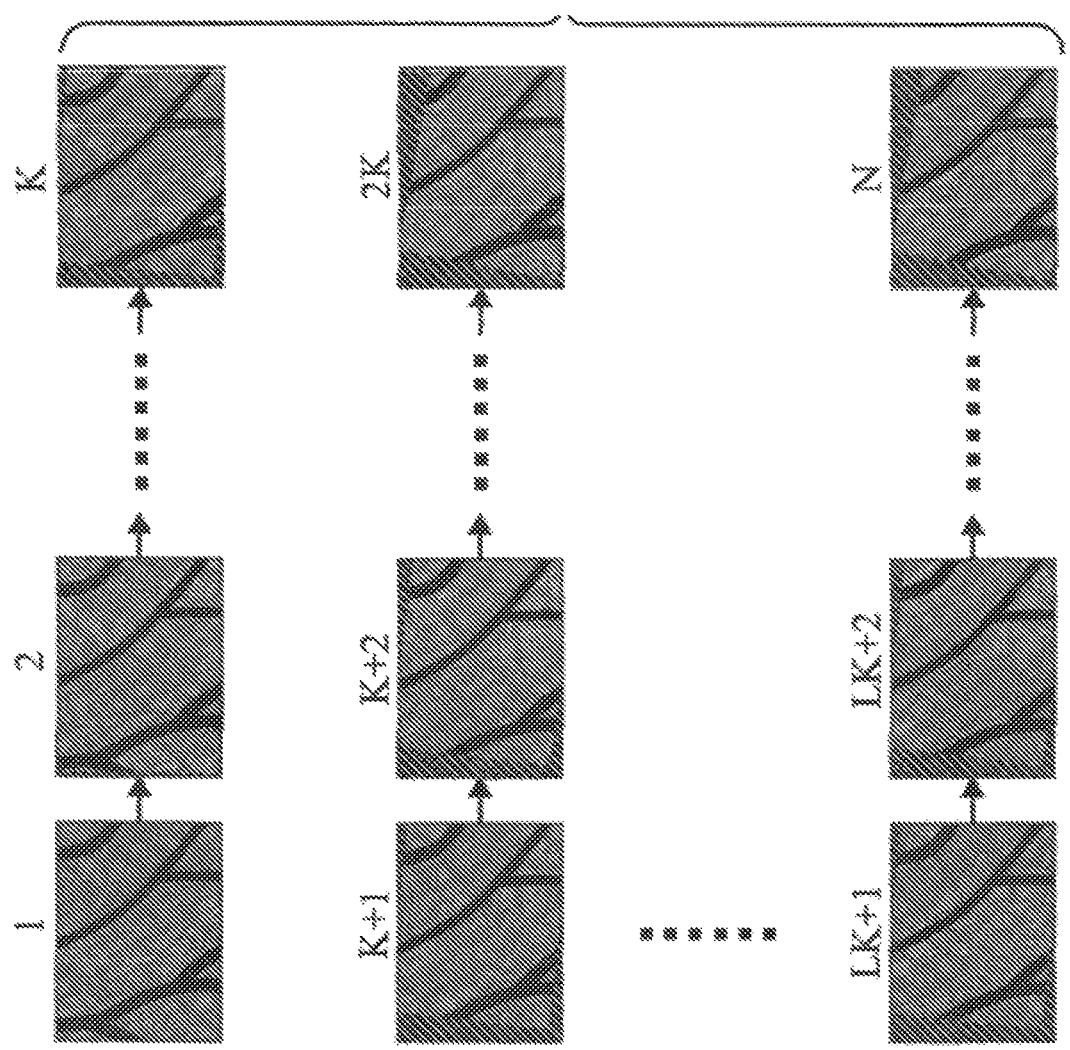
FIG. 4(b-3)

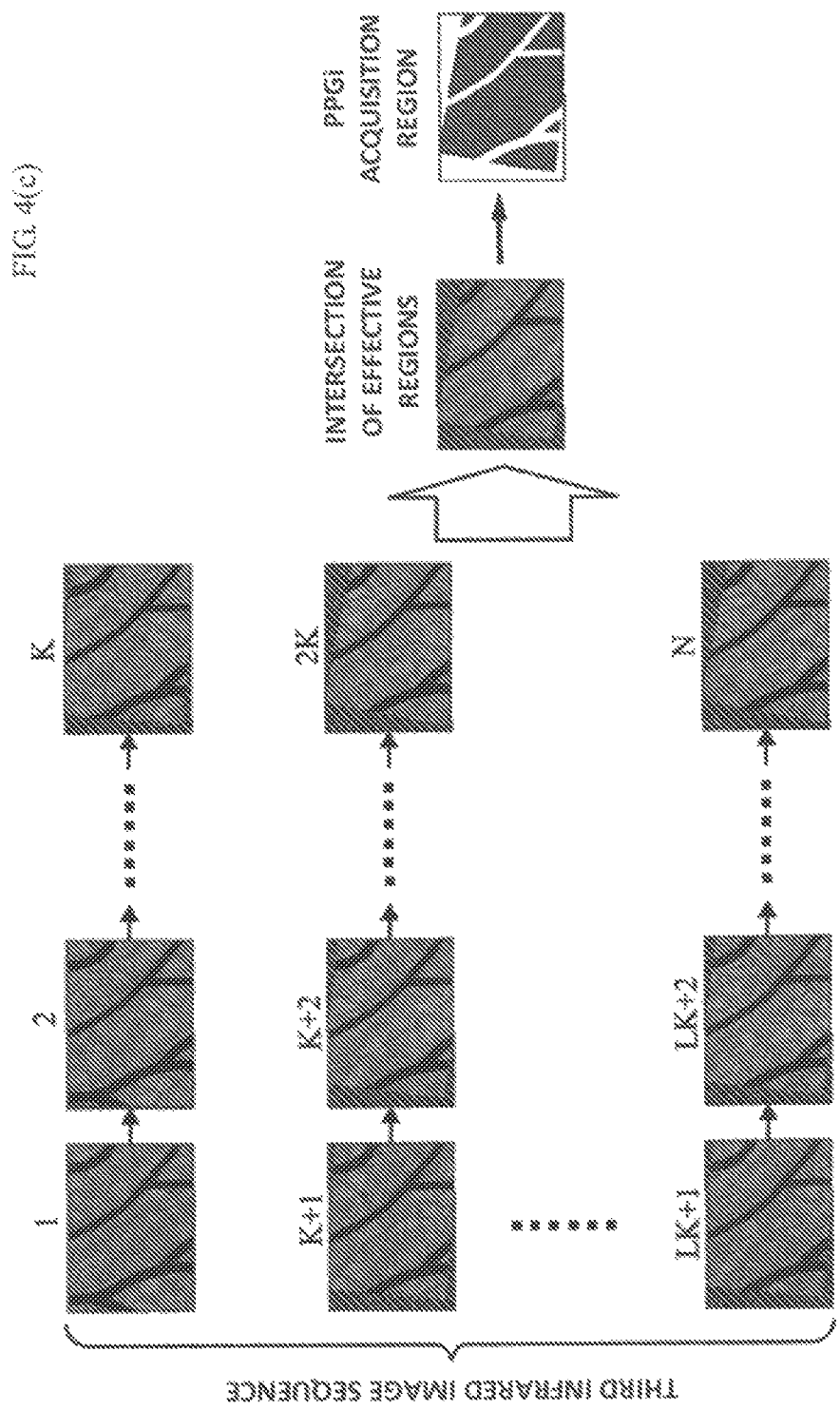

IMAGE INFORMATION GENERATION METHOD, PULSE WAVE MEASUREMENT SYSTEM AND ELECTRONIC DEVICE

CROSS-REFERENCE TO RELATED APPLICATIONS

This application is a U.S. National Stage under 35 U.S.C. § 371 of International Application No. PCT/CN2019/071772, filed on Jan. 15, 2019, which claims priority to Chinese Patent Application No. 201810671558.0, filed on Jun. 26, 2018, entitled "Image Information Generation Method, Pulse Wave Measurement and Electronic Device". The disclosure of each of these applications is incorporated by reference herein in its entirety.

TECHNICAL FIELD

The present disclosure relates to an image information generation method, a pulse wave measurement system and an electronic device.

BACKGROUND

Recently, photoplethysmography (PPG) and photoplethysmographic imaging (PPGi) are applied to perform pulse wave measurement. Basic principles of such methods are a Lamber-Beer law and a light scattering theory, a jump of a blood volume (i.e., a pulse wave) will cause a change in transmitted or scattered light of a corresponding part. In the PPG method, a photo sensor is used to measure a change in intensity of light transmitted through a target part or light reflected from the target part, to obtain a volume pulse wave; in the PPGi method, a camera is used to acquire an optical image of a light source transmitted or reflected via the target part, a degree of a change in color and/or luminance is analyzed through image processing, the volume pulse wave may be measured. Acquisition of the image or the light intensity has two forms of transmission and reflection: a method of acquiring transmitted light to perform imaging is applicable to a target part such as a finger, an earlobe, etc., with a small thickness, and with respect to a thick part such as a palm, etc., it is possible to adopt a method of acquiring reflected light to perform imaging.

SUMMARY

According to a first aspect of the present disclosure, there is provided an image information generation method comprising: with respect to a target part, acquiring a first infrared image sequence, each infrared image in the first infrared image sequence including at least a vein pattern; by registering the vein pattern in each infrared image in the first infrared image sequence, correcting each infrared image in the first infrared image sequence, thereby obtaining the corrected first infrared image sequence; removing at least the vein regions from respective infrared images in the corrected first infrared image sequence, to obtain image information of remaining regions as image information for pulse wave measurement.

In some embodiments, the step of, by registering the vein pattern in each infrared image in the first infrared image sequence, correcting each infrared image in the first infrared image sequence, thereby obtaining the corrected first infrared image sequence, comprises: selecting a reference image and a second infrared image sequence in the first infrared image sequence; recognizing vein patterns in respective infrared images in the second infrared image sequence; determining motions between vein patterns recognized in respective infrared images in the second infrared image sequence; based on the determined motions between vein patterns, correcting respective infrared images in the first infrared image sequence, to eliminate motions of respective infrared images relative to the reference image.

In some embodiments, the step of selecting the second infrared image sequence in the acquired first infrared image sequence comprises: dividing the first infrared image sequence into multiple groups in order, selecting the second infrared image sequence, so that respective infrared images of the second infrared image sequence are distributed in respective corresponding groups.

In some embodiments, in the second infrared image sequence, at least infrared images other than a last infrared image are selected at equal intervals from the first infrared image sequence.

In some embodiments, the motions include translation and rotation.

In some embodiments, the step of determining motions between vein patterns recognized in respective infrared images in the second infrared image sequence comprises: determining translation vectors and rotation angles between vein patterns in adjacent infrared images in the second infrared image sequence;

the step of, based on the determined motions between vein patterns, correcting respective infrared images in the first infrared image sequence, comprises: based on the determined translation vectors and rotation angles between vein patterns in respective pairs of adjacent infrared images in the second infrared image sequence, determining translation vectors and rotation angles of respective infrared images in the first infrared image sequence relative to the reference image, and accordingly translating and rotating respective infrared images in the first infrared image sequence.

In some embodiments, the image information generation method further comprises: before the step of removing at least the vein regions from respective infrared images in the corrected first infrared image sequence to obtain image information of remaining regions as image information for pulse wave measurement: obtaining an intersection of respective translated and rotated infrared images in the first infrared image sequence; and the step of removing at least the vein regions from respective infrared images in the corrected first infrared image sequence to obtain image information of remaining regions as image information for pulse wave measurement comprises: removing the vein regions from respective infrared images in the infrared image sequence after the intersection is obtained, to obtain image information of remaining regions as image information for pulse wave measurement.

In some embodiments, the step of selecting the reference image and the second infrared image sequence in the acquired first infrared image sequence comprises:

dividing the first infrared image sequence into L+1 groups, so that: (L+1)K≥N>LK, N is a number of the images of the first infrared image sequence, N, L and K are natural numbers;

when a last infrared image of the first infrared image sequence is a first infrared image of a last group, choosing first infrared images of respective groups to constitute the second infrared image sequence in order, otherwise, choosing first infrared images of respective groups and the last infrared image to constitute the second infrared image sequence in order;

selecting a first infrared image of the first infrared image sequence as the reference image.

In some embodiments, the step of, based on the determined translation vectors and rotation angles between vein patterns in respective pairs of adjacent infrared images in the second infrared image sequence, determining translation vectors and rotation angles of respective infrared images in the first infrared image sequence relative to the reference image, comprises: when the last infrared image of the first infrared image sequence is the first infrared image of the last group:

with respect to an infrared image with a number lK+k in the first infrared image sequence (l=0, 1, 2, . . . , L−1, k=1, 2, . . . , K), its translation vector $s_{lK+k}$ and rotation angle $\varphi_{lK+k}$ relative to the reference image are respectively:

$$\begin{cases} s_{lK+k} = \sum_{i=0}^{l} S_i + \frac{k-1}{K} S_{l+1} \\ \varphi_{lK+k} = \sum_{i=0}^{l} \Phi_i + \frac{k-1}{K} \Phi_{l+1} \end{cases}, S_0 \overset{def}{=} 0, \Phi_0 \overset{def}{=} 0,$$

wherein, $S_i$ denotes the translation vector between an ith pair of adjacent infrared images in the second infrared image sequence, $\Phi_i$ denotes the rotation angle between the ith pair of adjacent infrared images in the second infrared image sequence.

In some embodiments, the step of, based on the determined translation vectors and rotation angles between vein patterns in respective pairs of adjacent infrared images in the second infrared image sequence, determining translation vectors and rotation angles of respective infrared images in the first infrared image sequence relative to the reference image, comprises: when the last infrared image of the first infrared image sequence is not the first infrared image of the last group:

with respect to an infrared image with a number lK+k in the first infrared image sequence (l=0, 1, 2, . . . , L−1, k=1, 2, . . . , K), its translation vector $s_{lK+k}$ and rotation angle $\varphi_{lK+k}$ relative to the reference image are respectively:

$$\begin{cases} s_{lK+k} = \sum_{i=0}^{l} S_i + \frac{k-1}{K} S_{l+1} \\ \varphi_{lK+k} = \sum_{i=0}^{l} \Phi_i + \frac{k-1}{K} \Phi_{l+1} \end{cases}, S_0 \overset{def}{=} 0, \Phi_0 \overset{def}{=} 0;$$

with respect to an infrared image with a number LK+k in the first infrared image sequence (k=1, 2, . . . , N−LK), its translation vector $s_{lK+k}$ and rotation angle $\varphi_{lK+k}$ relative to the reference image are respectively:

$$\begin{cases} s_{LK+k} = \sum_{i=0}^{L} S_i + \frac{k-1}{N-LK-1} S_N \\ \varphi_{LK+k} = \sum_{i=0}^{L} \Phi_i + \frac{k-1}{N-LK-1} \Phi_N \end{cases}, S_0 \overset{def}{=} 0, \Phi_0 \overset{def}{=} 0,$$

wherein, $S_i$ denotes the translation vector between an ith pair of adjacent infrared images in the second infrared image sequence, $\Phi_i$ denotes the rotation angle between the ith pair of adjacent infrared images in the second infrared image sequence.

In some embodiments, K is ½ to ¼ of a frame rate of sampling of the first infrared image sequence.

In some embodiments, the step of correcting respective infrared images in the first infrared image sequence comprises: cutting out a part of the translated and rotated infrared image beyond a view range of the reference image, to obtain a corresponding corrected infrared image.

In some embodiments, the step of removing at least the vein regions from respective infrared images in the corrected first infrared image sequence to obtain image information of remaining regions as image information for pulse wave measurement comprises: determining a region of missing image information in the view range of the reference image in the corrected infrared image, and removing the region of the missing image information and the vein region, to obtain the remaining region.

In some embodiments, the method further comprises: performing image analysis on vein patterns recognized in at least one infrared image in the second infrared image sequence, to obtain pattern features for use in identity recognition.

In some embodiments, the method further comprises: using average values of luminance of remaining regions of respective infrared image to perform the pulse wave measurement.

According to a second aspect of the present disclosure, there is provided a pulse wave measurement system comprising: a near-infrared light source configured to irradiate a target part with infrared light; an infrared image acquisition device, configured to acquire an infrared image sequence of the target part, wherein each infrared image in the infrared image sequence includes at least a vein pattern; and a pulse wave measurement device, connected with the infrared image acquisition device communicatively, and including a processor, a memory and instructions stored thereon, when the processor executes the instructions, the processor implementing any one of the above mentioned image information generation methods, and using image information of remaining regions obtained by the method to perform the pulse wave measurement.

According to a third aspect of the present disclosure, there is provided an electronic device comprising: a processor; and a memory storing instructions, which when executed by the processor, cause the image processing device to perform the image information generation method as described above.

According to a fourth aspect of the present disclosure, there is provided a computer storage medium with computer-readable program instructions stored thereon which, when executed by a processor, cause the processor to perform the image information generation method as described above.

It is to be understood that, both the foregoing general description and the following detail description are only exemplary and illustrative, but are not used to limit the present disclosure.

This section provides a summary of various implementations or examples of technologies described in the present disclosure, and are not entire disclosure of all scopes or all features of the disclosed technologies.

BRIEF DESCRIPTION OF THE DRAWINGS

In order to explain technical solutions of embodiments of the present disclosure more clearly, accompanying drawings of the embodiments will be briefly introduced in the following. Evidently, the accompanying drawings in the following description relate to only some embodiments of the present disclosure, and do not limit the present disclosure.

FIG. 1 illustrates a flow chart of an image information generation method according to an embodiment of the present disclosure;

FIG. 4(a-1) to FIG. 4(a-2) and FIG. 4(b-1) to FIG. 4(b-3) illustrate an exemplary flow chart of a correction step in an image information generation method according to an embodiment of the present disclosure;

FIG. 4(c) illustrates an exemplary flow chart of an additional step executed before a vein region removal step in an image information generation method according to an embodiment of the present disclosure.

DETAILED DESCRIPTION

Figure 2:
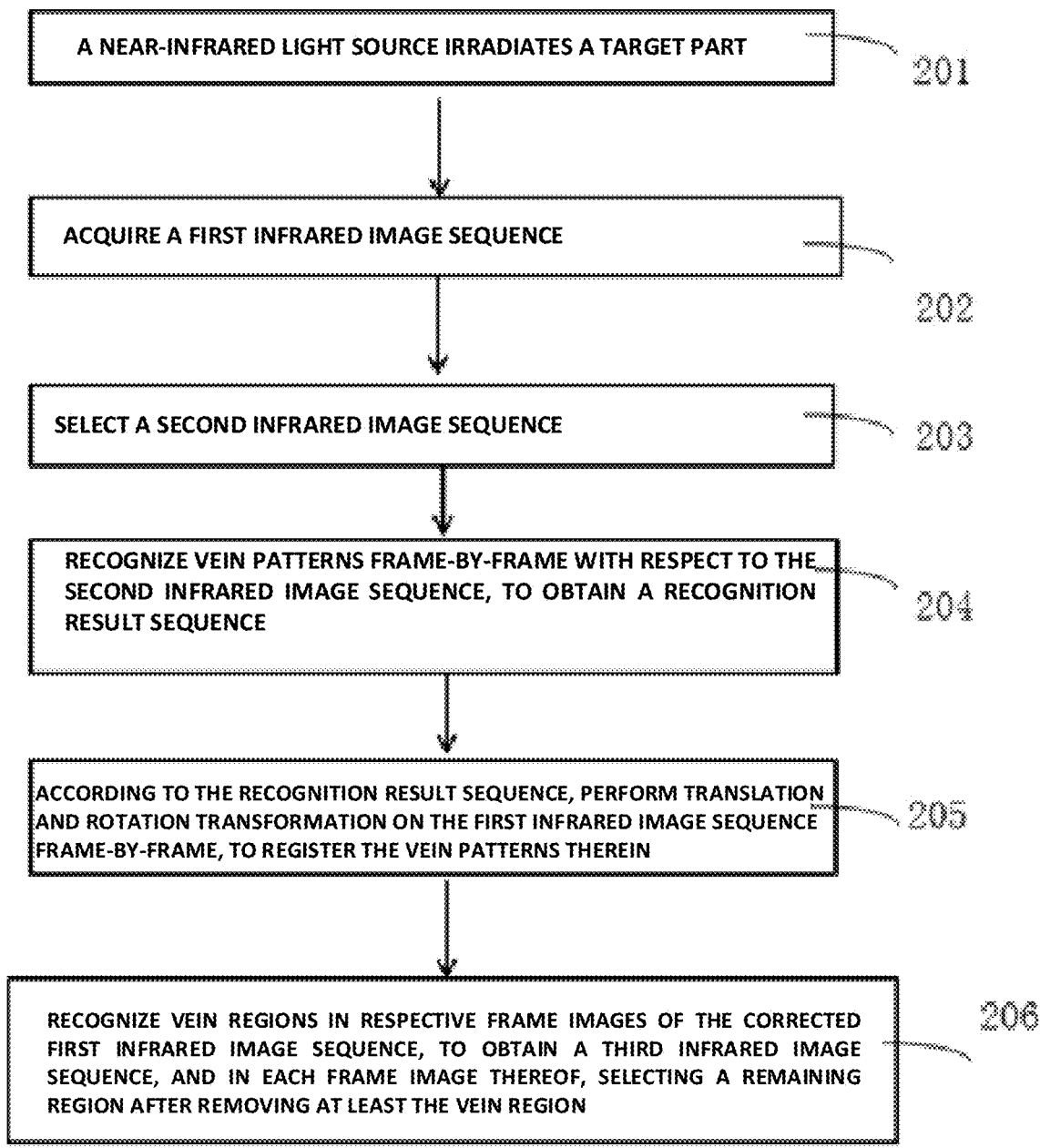
FIG. 2 illustrates a flow chart of an image information generation method according to another embodiment of the present disclosure.

In order to make objects, technical solutions and advantages of embodiments of the present disclosure more clear, a clear and complete description of technical solutions of embodiments of the present disclosure will be given below in conjunction with drawings of embodiments of the present disclosure. Obviously, described embodiments are a part of embodiments of the present disclosure, but not all of them. Based on the described embodiments of the present disclosure, all other embodiments obtained by those ordinary skilled in the art without creative labor fall within the protection scope of the present disclosure.

Unless defined otherwise, a technical term or a scientific term used by the present disclosure should have a general meaning as understood by those skilled in the art to which the present disclosure belongs. A term "first", "second" or a similar term used in the present disclosure does not refer to any order, quantity or importance, but is simply used to distinguish different constituent parts. A similar term such as a term "include" or "contain", etc, means that an element or object which appears before the term covers an element or object and equivalents thereof which appear and are listed after the term, but not preclude other elements or objects. In order to make the following explanation of embodiments of the present disclosure clear and brief, the present disclosure omits a detailed explanation of known functions and known components.

Generally, a pulse wave measurement apparatus and a vein recognition apparatus are separate. A user generally needs two independent apparatuses to achieve pulse wave measurement and vein recognition, respectively, this results in a low integration level of apparatuses, occupies a relatively large space, and is disadvantageous to miniaturization of apparatuses.

In a current pulse wave measurement method and apparatus, a change in thickness of a vein is discriminated from infrared images of the vein acquired continuously, to detect the pulse wave, and improvements on pulse wave detection also concentrate on such as image enlargement, edge extraction. But reflection of the pulse wave on the change in thickness of the vein is too weak to be discriminated and detected, which influences a detection accuracy and a sensitivity of the pulse wave. And, in a process of acquiring an infrared image sequence of a target part, motion generally occurs, so that this interferes with a detection result, further influences the detection accuracy of the pulse wave. Another aspect of the present disclosure is to provide an improved image information generation method, the method can apply vein recognition to pulse wave measurement, generate image information that can significantly show the change in the pulse wave, and can eliminate an error caused by motion, thereby improve the detection accuracy and the sensitivity of the pulse wave.

Another aspect of the present disclosure is to provide an improved pulse wave measurement system, the system can integrate a vein recognition device and a pulse wave measurement device, share a near-infrared light source and an infrared image acquisition device, improve an integration level and reduce an volume, be advantageous to miniaturization of apparatuses; and, it uses a result of the vein recognition device to improve the detection accuracy and the sensitivity of the pulse wave of the pulse wave measurement device.

FIG. 1 illustrates a flow chart of an image information generation method according to an embodiment of the present disclosure, the method comprises: with respect to a target part, acquiring a first infrared image sequence, each infrared image in the first infrared image sequence including at least a vein pattern (an acquisition step 101); by registering the vein pattern in each infrared image in the first infrared image sequence, correcting each infrared image in the first infrared image sequence, thereby obtaining the corrected first infrared image sequence (a correction step 102); removing at least the vein regions from respective infrared images in the corrected first infrared image sequence, to obtain image information of remaining regions as image information for pulse wave measurement (a vein region removal step 103).

In the infrared image, the vein pattern is generally stable with respect to the target part, thus motion of the vein pattern shows the target part, the method, by registering vein patterns in respective infrared images, can correct respective infrared images and eliminate motion errors, thereby improve the accuracy of the pulse wave measurement. And by removing at least vein regions from respective corrected infrared images, the obtained remaining region no longer includes the vein region, image information for the pulse wave measurement mainly originates from image information of an artery region, and considering that a change in image information caused by the pulse wave in the artery region, e.g., but not limited to, a change in an outline, a change in a diameter, a change in a luminance in the region, a change in a grayscale in the region, a change in a color in the region (presenting the infrared image as a heat map), etc, is much more obvious than that in the vein region, thus the sensitivity of the pulse wave measurement is further improved. It is noted that, in the present disclosure, a technical term "image information of the remaining region" includes information of image parameters of the remaining region, also includes an image obtained after removing at least the vein region. It is possible to use a sequence of images obtained after removing at least the vein regions to obtain the pulse wave.

The correction step 102 may be achieved by various methods, e.g. it is possible to mark several pixels of vein patterns in respective infrared images, use an optical flow algorithm to compute frame-by-frame motion vectors of these corresponding pixels of the vein patterns, and accordingly correct respective infrared images, such that these corresponding pixels in the vein patterns in respective corrected infrared images are aligned. The optical flow algorithm computes the motion vectors frame-by-frame, an registration result between two adjacent frames is good, but the amount of computation is large, requirements for a processor are high and a long time is taken, and correspondingly, a cost of the pulse wave measurement device is also increased.

In some embodiments, there is provided a correction method which performs more convenient computation, consumes less resources, also takes a shorter time, the method includes: selecting a reference image and a second infrared image sequence in the first infrared image sequence; recognizing vein patterns in respective infrared images in the second infrared image sequence; determining motions between vein patterns recognized in respective infrared images in the second infrared image sequence; based on the determined motions between vein patterns, correcting respective infrared images in the first infrared image sequence, to eliminate their motions relative to the reference image. By selecting a partial image sequence as the second infrared image sequence from the first infrared image sequence according to a certain rule, both recognition of vein patterns and determination of relative motion between vein patterns are only confined to the second infrared image sequence, and in comparison with frame-by-frame computation of the optical flow method, this significantly reduces the amount of computation. Further, since the second infrared image sequence is distributed in the first infrared image sequence, time intervals between respective infrared images thereof are relatively short, several infrared images in the second infrared image sequence are located between the infrared image to be corrected and the reference image, thus correction can be performed stepwise relative to the reference image. Considering that, upon the pulse wave measurement, generally the degree of freedom of motion of the target part is limited, the motion is relatively slow, the motion is uniform in a short time period, such a stepwise correction method complies with actual motion characteristics better, an effect of eliminating motion interferences is relatively good.

In some embodiments, the step of selecting the second infrared image sequence in the acquired first infrared image sequence comprises: dividing the first infrared image sequence into multiple groups in order, selecting the second infrared image sequence, so that respective infrared images thereof are distributed in respective corresponding groups. As such, each group corresponds to a relatively short time period in which the motion of the target part is relatively uniform, so that respective infrared images of the second infrared image sequence are distributed in respective corresponding groups, so that motions between vein patterns recognized in respective infrared images in the second infrared image sequence can fully represent motion characteristics in respective relatively short time periods, the effect of eliminating motion interferences is better.

In some embodiments, in the second infrared image sequence, at least infrared images other than a last infrared image are selected at equal intervals from the first infrared image sequence. Such a method of selecting the second infrared image sequence at equal intervals simplifies operations of selection and correction of the second infrared image sequence.

In some embodiments, the motions are simplified as translation and rotation. Thus, the step of determining motions between vein patterns recognized in respective infrared images in the second infrared image sequence comprises: determining translation vectors and rotation angles between vein patterns in adjacent infrared images in the second infrared image sequence; the step of, based on the determined motions between vein patterns, correcting respective infrared images in the first infrared image sequence, comprises: based on the determined translation vectors and rotation angles between vein patterns in respective pairs of adjacent infrared images in the second infrared image sequence, determining translation vectors and rotation angles of respective infrared images in the first infrared image sequence relative to the reference image, and accordingly translating and rotating respective infrared images in the first infrared image sequence. An infrared image generally may be expressed as a two-dimensional matrix, both computing a translation vector and a rotation angle between two-dimensional matrixes and performing translation and rotation operations on the two-dimensional matrix are relatively simple, and there is an effect of acceleration, so that the effect of eliminating motion interferences effectively is achieved with a lower amount of computation and with less consumed time.

FIG. 2 illustrates a flow chart of an image information generation method according to another embodiment of the present disclosure. The image information generation method comprises the following steps.

step 201: using a near-infrared light source to irradiate a target part to be acquired.

step 202: using an infrared image acquisition device to continuously acquire infrared images of the target part which include at least an artery and a vein, to obtain a continuous first infrared image sequence. The continuous infrared image sequence i.e., a video, is a series of infrared images ordered according to a photographing time, each infrared image is one frame of the video.

step 203: from the first infrared image sequence, selecting a part of images according to a certain law and ordering them according to the photographing time as a second infrared image sequence.

step 204: recognizing vein patterns frame-by-frame with respect to the second infrared image sequence, to obtain a recognition result sequence.

step 205: according to the recognition result sequence, performing translation and rotation transformation on the first infrared image sequence frame-by-frame, to register the vein patterns therein, thus correct the first infrared image sequence to a same motion phase and eliminate motion errors between respective frames thereof.

step 206: recognizing vein regions in respective frame images of the corrected first infrared image sequence, to obtain a third infrared image sequence, and in each frame image thereof, selecting a remaining region after removing at least the vein region. As such, it is possible to measure a degree of the image intensity change within the remaining region on each frame, as a waveform of the photo volume pulse wave.

In some embodiments, an active method of irradiating with an infrared light source is used to achieve the vein imaging. Specifically, an absorption characteristic of hemoglobin in the vein with respect to near-infrared rays of a specific wavelength range (690 nm~980 nm) is used to perform imaging, an absorption coefficient of water within the wave band is low, an absorption coefficient of hemoglobin is significantly higher than that of other subcutaneous tissues. Therefore, near-infrared rays reflected by or transmitted via the vein are less than those reflected by or transmitted via muscles or skeletons, so that an infrared image of the vein may be well distinguished from a surrounding background image, and it is expressed as an obvious dark part in the infrared image acquired by the infrared image acquisition device.

Figure 3:
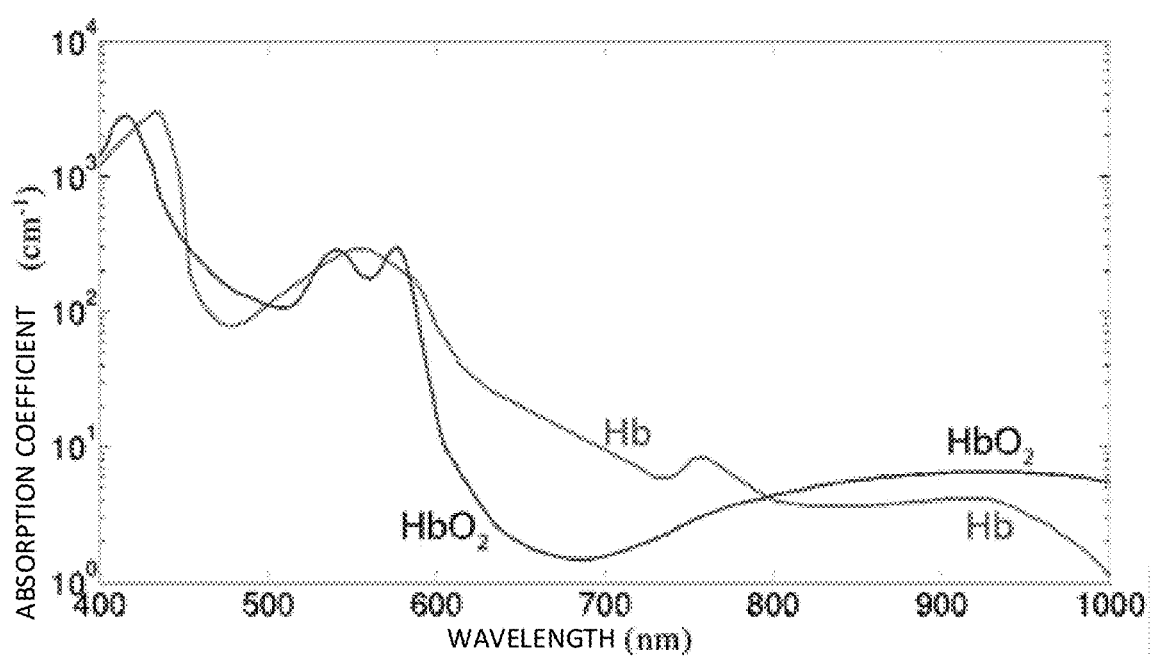
FIG. 3 illustrates a graph in which absorption coefficients of a deoxyhemoglobin and an oxyhemoglobin change with a wavelength.

In some embodiments, a wavelength of the near-infrared light source in step 201 may be set to be near 760 nm, e.g. 740 nm-780 nm. As shown in FIG. 3, near a wavelength of 760 nm, an absorption coefficient of deoxyhemoglobin is significantly higher than that of oxyhemoglobin, and in the infrared image, in comparison with the artery, the vein appears as an obvious dark part; meanwhile, near the wavelength of 760 nm, the absorption coefficient of oxyhemoglobin is still higher than that of moisture and other surrounding tissues, the PPGi method can work effectively. By setting the wavelength to be near 760 nm, this can improve an accuracy and a sensitivity of recognizing the vein patterns, so that this ensures that the image intensity change for the PPGi method is confined to a non-vein region, e.g. an artery region in which image information significantly changes with the pulse wave, thus improves the accuracy and the sensitivity of the pulse wave measurement.

In some embodiments, in step 202, a frame rate of acquiring the continuous infrared images is not lower than 8 frames/second. The present inventor has found that, frequency components in the photo volume pulse wave which include valuable information is mainly in 0~4 Hz, and by adopting a sampling rate not lower than 8 Hz, according to the Nyquist theorem, a digital signal after sampling fully retains information in an original signal.

One embodiment of steps 203-204 is as shown in FIG. 4(a1) to FIG. 4(a-2). It is assumed that the first infrared image sequence includes N (N is a natural number) infrared images, chronologically numbered as 1, 2, . . . , N. It may be seen that, because of the motion of the target part in the process of acquisition, position and angle differences occur between the acquired images (especially vein patterns).

A suitable natural number K is chosen, the first infrared image sequence is divided into L+1 groups, K and L satisfy a formula (1) below:

$$(L+1)K \geq N > LK \qquad \text{formula (1)}$$

That is, each of a 1st group to an Lth group includes K infrared images, a (L+1)th group includes 1 to K infrared images. A numerical value of L is decided by K, a value range of K is preferably ½-¼ of the frame rate of sampling. The bigger the value of K, the smaller the amount of computation of step 203; the smaller the value of K, the better the effect of eliminating motion errors.

In some embodiments, after the first infrared image sequence is grouped in the above mentioned method, it is possible to select the second infrared image sequence from it according to the following steps:

(1) if N=LK+1, i.e., when the last infrared image of the first infrared image sequence is the first infrared image of the last group, choosing infrared images with numbers lK+1 (l=0, 1, 2, . . . , L) (i.e. first infrared images of respective groups), and chronologically arranging them as the second infrared image sequence, the second infrared image sequence obtained as such including L+1 infrared images;

(2) if N≠LK+1, i.e., when the last infrared image of the first infrared image sequence is not the first infrared image of the last group, choosing infrared images with numbers lK+1 (l=0, 1, 2, . . . , L) and an infrared image with a number N, and chronologically arranging them as the second infrared image sequence, the second infrared image sequence obtained as such including L+2 infrared images; as shown in FIG. 4(a-1) to FIG. 4(a-2).

Each frame image in the first infrared image sequence and the second infrared image sequence includes a vein and other tissues, wherein the image intensity of the vein is significantly lower than that of other tissues. In the above mentioned step 204, vein recognition is performed on the second infrared image sequence frame-by-frame, so that vein patterns are recognized. In some embodiments, it is possible to perform image analysis on vein patterns recognized in at least one infrared image in the second infrared image sequence, to obtain pattern features for use in identity recognition. The vein pattern of each individual is different, and thus, while vein pattern recognition is performed for the pulse wave measurement, identity recognition can be achieved based on pattern features thereof, a user's privacy is ensured effectively. Accordingly, in the recognition result sequence obtained in step 204, each recognition result includes a vein pattern and also includes image features extracted.

One embodiment of steps 205-206 is as shown in FIG. 4(b-1) to FIG. 4(b-3). According to the recognition result sequence:

(3) if N=LK+1 (at this time, L is certainly more than 0), comparing recognition results of infrared images with their respective numbers being lK+1 and (l−1)K+1 (wherein l=1, 2, . . . , L) (i.e., an lth pair of adjacent infrared images in the second infrared image sequence) in order, obtaining: relative to the vein pattern in the infrared image with the number (l−1)K+1, the vein pattern in the infrared image with the number lK+1 translates by a vector $S_l$, rotates by an angle $\Phi_l$ (wherein l=1, 2, . . . , L) anticlockwise.

(4) if N≠K+1, on a basis of (3), additionally measuring that, relative to the vein image in the infrared image with the number LK+1, the vein image in the infrared image with the number N translates by a vector $S_N$, rotates by an angle $\Phi_N$ anticlockwise.

In some embodiments, the method of obtaining the above mentioned translation vectors and rotation angles includes but not limited to any one or more of image cross-correlation, template matching and feature point matching.

In some embodiments, a translation vector and a rotation angle of an infrared image located between a certain pair of adjacent infrared images in the second infrared image sequence relative to a former image in the pair of infrared images can be computed based on an average translation speed and an average rotation angular speed in the period of time. In fact, the infrared image acquisition device often has one bracket which holds the target part or a transparent plane which supports the target part, the degree of freedom of the motion of the target part is limited, the target part generally moves within a plane which is perpendicular to a direction of an optical axis of the camera device, the motion is relatively slow. Therefore, in a short period of time between an lth pair of adjacent infrared images in the second infrared image sequence, it is possible to consider the motion of the target part to be uniform, the above computation based on the average translation speed and the average rotation angular speed in the period of time complies with a real motion state of the target part, the precision is relatively high.

In the first infrared image sequence, from the infrared image with the number (l−1)K+1 to the infrared image with the number lK+1, whenever passing one frame, the vein pattern translates by a vector $1/K \cdot S_l$, rotates by an angle $1/K \cdot \Phi_l$ anticlockwise relative to a first infrared image. As an example, in the following explanation, an infrared image with a number 1 (i.e. the first infrared image in the first infrared image sequence) is adopted as the reference image. Therefore, a translation vector and a rotation angle of any one frame in the first infrared image sequence relative to the infrared image with the number 1 are as follows.

(5) when the last infrared image of the first infrared image sequence is the first infrared image of the last group:

with respect to an infrared image with a number lK+k in the first infrared image sequence (l=0, 1, 2, ..., L−1, k=1, 2, ..., K), its translation vector $s_{lK+k}$ and rotation angle $\varphi_{lK+k}$ relative to the reference image are respectively:

$$\begin{cases} s_{lK+k} = \sum_{i=0}^{l} S_i + \frac{k-1}{K} S_{l+1} \\ \varphi_{lK+k} = \sum_{i=0}^{l} \Phi_i + \frac{k-1}{K} \Phi_{l+1} \end{cases}, S_0 \stackrel{def}{=} 0, \Phi_0 \stackrel{def}{=} 0, \quad \text{formula (2)}$$

wherein, $S_i$ denotes the translation vector between an ith pair of adjacent infrared images in the second infrared image sequence, $\Phi_i$ denotes the rotation angle between the ith pair of adjacent infrared images in the second infrared image sequence.

(6) when the last infrared image of the first infrared image sequence is not the first infrared image of the last group:

with respect to an infrared image with a number lK+k in the first infrared image sequence (l=0, 1, 2, ..., L−1, k=1, 2, ..., K), its translation vector $s_{lK+k}$ and rotation angle $\varphi_{lK+k}$ relative to the reference image are respectively:

$$\begin{cases} s_{lK+k} = \sum_{i=0}^{l} S_i + \frac{k-1}{K} S_{l+1} \\ \varphi_{lK+k} = \sum_{i=0}^{l} \Phi_i + \frac{k-1}{K} \Phi_{l+1} \end{cases}, S_0 \stackrel{def}{=} 0, \Phi_0 \stackrel{def}{=} 0;$$

with respect to an infrared image with a number LK+k in the first infrared image sequence (k=1, 2, ..., N−LK), its translation vector $s_{lK+k}$ and rotation angle $\varphi_{lK+k}$ relative to the reference image are respectively:

$$\begin{cases} s_{LK+k} = \sum_{i=0}^{L} S_i + \frac{k-1}{N-LK-1} S_N \\ \varphi_{LK+k} = \sum_{i=0}^{L} \Phi_i + \frac{k-1}{N-LK-1} \Phi_N \end{cases}, S_0 \stackrel{def}{=} 0, \Phi_0 \stackrel{def}{=} 0,$$

wherein, $S_i$ denotes the translation vector between an ith pair of adjacent infrared images in the second infrared image sequence, $\Phi_i$ denotes the rotation angle between the ith pair of adjacent infrared images in the second infrared image sequence.

According to formulas (5) and/or (6), the translation vector and the anticlockwise rotation angle of each frame infrared image in the first infrared image sequence relative to the infrared image with the number 1 are computed, and as shown in FIG. 4(b-1) to FIG. 4(b-3), a view range corresponding to the infrared image with the number 1 is taken as a reference, each frame infrared image is rotated and translated to the same position and angle as the infrared image with the number 1, to obtain the third infrared image sequence.

FIG. FIG. 4(b-1) to FIG. 4(b-3) illustrate one embodiment of step 206.

Specifically, because of the motion of the acquired target part, in the course of the rotation and the movement, other frame infrared images will have parts which go beyond the view range of the infrared image with the number 1, these parts of the images are cut out, as shown in FIG. FIG. 4(b-1) to FIG. 4(b-3). In the view range of the infrared image with the number 1, there is probably a part of image information missing in other frame infrared images, this part of view is recognized, e.g. such as shown in FIG. FIG. 4(b-1) to FIG. 4(b-3), is marked as a shaded part. As such, within the non-shaded view range, the vein pattern in each frame infrared image in the third infrared image sequence can overlap with each other.

Further, if the first infrared image sequence is only a part of infrared images of the acquire target part, i.e., the view of the infrared image acquisition device is larger than the views corresponding to the images in the first infrared image sequence, the processes of cutting out and marking may be partially or wholly omitted.

In some embodiments, a region outside the marked part (the shaded part in FIG. 4(c)) in each frame in the third infrared image sequence is an effective image region, and according to these effective image regions, an intersection region of effective image regions of all frames is computed (or a union set of the marked parts is computed and all shaded parts are removed), as shown in FIG. 4(c). Within the intersection region, each frame in the third infrared image sequence has an effective infrared image. According to the result of the vein recognition, the vein region is removed from the intersection region, the obtained region is the remaining region in step 206 as the acquisition region in which the PPGi method is applied (as shown in FIG. 4(c)). It is noted that "vein region" mentioned in the present disclosure refers to an image region containing the vein pattern, e.g. it may be a region constituted by a peripheral envelope of the vein pattern.

The change in the image intensity within the acquisition region is mainly caused by arterial pulses. It is possible to apply the PPGi method to the acquisition region, e.g.: an average luminance value within the remaining region in each frame in the third infrared image sequence is detected, as a measurement result of the photo volume pulse wave.

In the above mentioned process of rotation and movement, the infrared image with the number 1 is exemplarily taken as the reference. Since the relative relationship between this series of infrared images has transitivity, in other implementations of the method, it is also possible to take any one frame as the reference.

Figure 5:
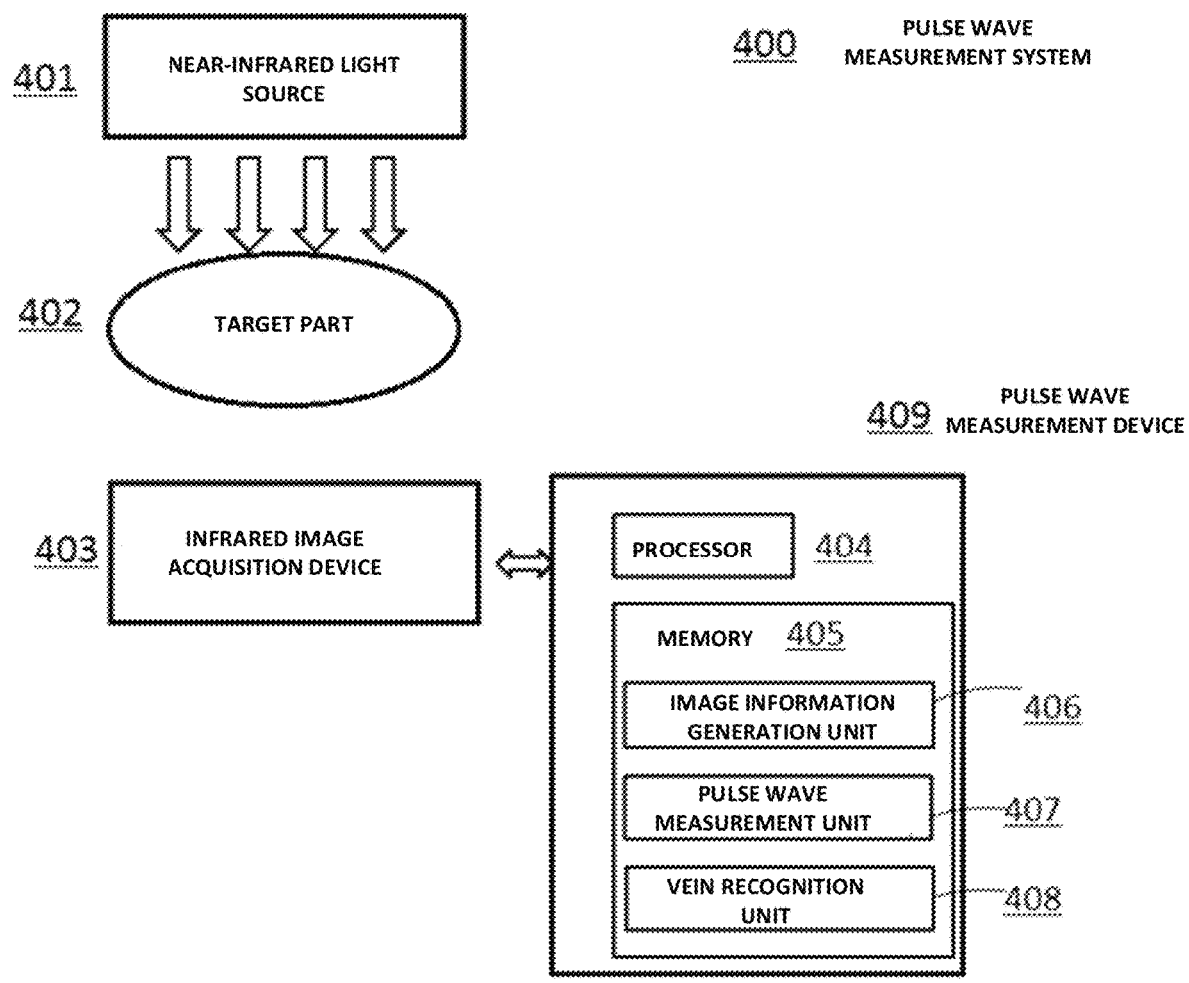
FIG. 5 illustrates a schematic view of a pulse wave measurement system according to an embodiment of the present disclosure.

In some embodiments of the present disclosure, there is provided a pulse wave measurement system 400. As shown in FIG. 5, the pulse wave measurement system 400 includes: a near-infrared light source 401 configured to irradiate a target part 402 with infrared light; an infrared image acquisition device 403 configured to acquire an infrared image sequence of the target part which includes at least an artery and a vein; and a pulse wave measurement device 409, connected with the infrared image acquisition device 403 communicatively, and including a processor 404, a memory 405 and instructions stored thereon, when the processor 404 executes the instructions, the processor 404 implementing any of the aforementioned generating image information methods for pulse wave measurement, and using image information of remaining regions obtained by the method to perform the pulse wave measurement. These instructions may constitute respective software modules, including an image information generation unit 406, a pulse wave measurement unit 407 and a vein recognition unit 408, etc. Wherein, the image information generation unit 406 is configured to achieve aforementioned any method of generating image information for pulse wave measurement; the pulse wave measurement unit 407 is configured to use the image information generated by the image information generation unit 406 to measure the pulse wave; the vein recognition unit 408 is configured to recognize the vein pattern in the infrared image and feed the recognition result to the image information generation unit 406.

The near-infrared light source 401 and the infrared image acquisition device 403 of the system 400 are used for both the pulse wave measurement and the vein recognition, the system integrates the vein recognition device and the pulse wave measurement device, improves an integration level and reduce an volume, is advantageous to miniaturization of apparatuses; and, it uses the result of the vein recognition device to improve the detection accuracy and the sensitivity of the pulse wave of the pulse wave measurement device.

In some embodiments, the wavelength of the infrared light irradiated by the near-infrared light source is near 760 nm, to improve the contrast between the vein region and the artery region, thereby facilitate the vein recognition.

In some embodiments, the frame rate of acquisition of the infrared image acquisition device is not lower than 8 frames/second, so that this ensures that the sampling does not lose useful information in original signals.

The memory 405 may take various forms, including but not limited to e.g. a volatile memory and/or a nonvolatile memory. The volatile memory, e.g., may include a random access memory (RAM) and/or a cache, etc. The nonvolatile memory, e.g., may include a read-only memory (ROM), a hard disk, an erasable programmable read-only memory (EPROM), a portable compact disc read-only memory (CD-ROM), a USB memory, a Flash memory, etc.

The processor 404 may be a processing device, including one or more general-purpose process devices, e.g. a microprocessor, a central processing unit (CPU), a graphics processing unit (GPU), an accelerated processing unit (APU), etc. More specifically, the processor 404 may be a complex instruction set computing (CISC) microprocessor, a reduced instruction set computing (RISC) microprocessor, a very long instruction word (VLIW) microprocessor, a processor implementing other instruction sets, or a processor implementing a combination of instruction sets. The processor 404 may also be one or more special-purpose processing devices such as an application specific integrated circuit (ASIC), a field programmable gate array (FPGA), a digital signal processor (DSP), a system on chip (SOC), or the like. As will be appreciated by those skilled in the art, in some embodiments, the processor 404 may be a special-purpose processor but not a general-purpose processor. The processor 204 may include one or more known process devices, e.g., a microprocessor from a family of Pentium™, Core™, Xeon™ or Itanium® manufactured by Intel™, a microprocessor from a family of Turion™, Athlon™, Sempron™, Opteron™, FX™, Phenom™ manufactured by AMD™, or any of various processors manufactured by Sun Microsystems. The processor 204 may also include the accelerated processing unit. The disclosed embodiment is not limited to any type of (one or more) processors, the processors are configured, in other ways, to satisfy computation demands of recognizing, analyzing, keeping, generating and/or providing a large amount of image data or processing such image data, or configured, in other ways, to process any other type of data consistent with the disclosed embodiment. In addition, the term "processor" may include more than one processor, e.g. a multi-core design or multiple processors with the multi-core design.

The above embodiments are only exemplary embodiments of the present invention, are not used to limit the present invention, a protection scope of the present invention is defined by claims. Within the substance and the protection scope of the present invention, those skilled in the art may make various modifications or equivalent substitutions to the present invention, such modifications or equivalent substitutions are also to be considered to fall within the protection scope of the present invention.

What is claimed is:

1. An image information generation method comprising:
   with respect to a target part, acquiring a first infrared image sequence, each infrared image in the first infrared image sequence including at least a vein pattern;
   by registering the vein pattern in each infrared image in the first infrared image sequence, correcting each infrared image in the first infrared image sequence, thereby obtaining a corrected first infrared image sequence; and
   removing at least vein regions from respective infrared images in the corrected first infrared image sequence, to obtain image information of remaining regions as image information for pulse wave measurement.

2. The image information generation method according to claim 1, wherein the step of, by registering the vein pattern in each infrared image in the first infrared image sequence, correcting each infrared image in the first infrared image sequence, thereby obtaining the corrected first infrared image sequence, further comprises:
   selecting a reference image and a second infrared image sequence in the first infrared image sequence;
   recognizing vein patterns in respective infrared images in the second infrared image sequence;
   determining motions between vein patterns recognized in respective infrared images in the second infrared image sequence; and
   based on the determined motions between vein patterns, correcting respective infrared images in the first infrared image sequence, to eliminate motions of respective infrared images relative to the reference image.

3. The image information generation method according to claim 2, wherein the step of selecting the second infrared image sequence in the acquired first infrared image sequence further comprises: dividing the first infrared image sequence into multiple groups in order, selecting the second infrared image sequence, so that respective infrared images of the second infrared image sequence are distributed in respective corresponding groups.

4. The image information generation method according to claim 3, wherein in the second infrared image sequence, at least infrared images other than a last infrared image are selected at equal intervals from the first infrared image sequence.

5. The image information generation method according to claim 4, wherein the motions include translation and rotation.

6. The image information generation method according to claim 5, wherein the step of determining motions between vein patterns recognized in respective infrared images in the second infrared image sequence comprises: determining translation vectors and rotation angles between vein patterns in adjacent infrared images in the second infrared image sequence;
   the step of, based on the determined motions between vein patterns, correcting respective infrared images in the first infrared image sequence, comprises: based on the determined translation vectors and rotation angles between vein patterns in respective pairs of adjacent infrared images in the second infrared image sequence, determining the translation vectors and rotation angles of respective infrared images in the first infrared image sequence relative to the reference image, and accordingly translating and rotating respective infrared images in the first infrared image sequence.

7. The image information generation method according to claim 6, wherein the image information generation method further comprises: before the step of removing at least the vein regions from respective infrared images in the corrected first infrared image sequence to obtain image information of remaining regions as image information for pulse wave measurement: obtaining an intersection of respective translated and rotated infrared images in the first infrared image sequence; and the step of removing at least the vein regions from respective infrared images in the corrected first infrared image sequence to obtain image information of remaining regions as image information for pulse wave measurement further comprises: removing the vein regions from respective infrared images in the first infrared image sequence after the intersection is obtained, to obtain image information of remaining regions as image information for pulse wave measurement.

8. The image information generation method according to claim 7, further comprising: using average values of luminance of remaining regions of respective infrared images for the pulse wave measurement.

9. The image information generation method according to claim 6, wherein the step of selecting the reference image and the second infrared image sequence in the acquired first infrared image sequence comprises:

dividing the first infrared image sequence into L+1 groups, so that: (L+1)K≥N>LK, N is a number of the images of the first infrared image sequence, N, L and K are natural numbers;

when a last infrared image of the first infrared image sequence is a first infrared image of a last group, choosing first infrared images of respective groups to constitute the second infrared image sequence in order, otherwise, choosing first infrared images of respective groups and the last infrared image to constitute the second infrared image sequence in order;

selecting the first infrared image of the first infrared image sequence as the reference image.

10. The image information generation method according to claim 9, wherein the step of, based on the determined translation vectors and rotation angles between vein patterns in respective pairs of adjacent infrared images in the second infrared image sequence, determining translation vectors and rotation angles of respective infrared images in the first infrared image sequence relative to the reference image, further comprises: when the last infrared image of the first infrared image sequence is the first infrared image of the last group:

with respect to an infrared image with a number lK+k in the first infrared image sequence (l=0, 1, 2, . . . , L−1, k=1, 2, . . . , K), translation vector $s_{lK+k}$ and and rotation angle $\varphi_{lK+k}$ relative to the reference image are respectively:

$$\begin{cases} s_{lK+k} = \sum_{i=0}^{l} S_i + \frac{k-1}{K} S_{l+1} \\ \varphi_{lK+k} = \sum_{i=0}^{l} \Phi_i + \frac{k-1}{K} \Phi_{l+1} \end{cases}, S_0 \stackrel{def}{=} 0, \Phi_0 \stackrel{def}{=} 0,$$

wherein, $S_i$ denotes the translation vector between an ith pair of adjacent infrared images in the second infrared image sequence, $\varphi_i$ denotes the rotation angle between the ith pair of adjacent infrared images in the second infrared image sequence.

11. The image information generation method according to claim 9, wherein the step of, based on the determined translation vectors and rotation angles between vein patterns in respective pairs of adjacent infrared images in the second infrared image sequence, determining translation vectors and rotation angles of respective infrared images in the first infrared image sequence relative to the reference image, comprises: when the last infrared image of the first infrared image sequence is not the first infrared image of the last group:

with respect to an infrared image with a number lK+k in the first infrared image sequence (l=0, 1, 2, . . . , L−1, k=1, 2, . . . , K), translation vector $s_{lK+k}$ and rotation angle $\varphi_{lK+k}$ relative to the reference image are respectively:

$$\begin{cases} s_{lK+k} = \sum_{i=0}^{l} S_i + \frac{k-1}{K} S_{l+1} \\ \varphi_{lK+k} = \sum_{i=0}^{l} \Phi_i + \frac{k-1}{K} \Phi_{l+1} \end{cases}, S_0 \stackrel{def}{=} 0, \Phi_0 \stackrel{def}{=} 0;$$

with respect to an infrared image with a number LK+k in the first infrared image sequence (k=1, 2, . . . , N−LK), translation vector $s_{lK+k}$ and rotation angle $\varphi_{lK+k}$ relative to the reference image are respectively:

$$\begin{cases} s_{LK+k} = \sum_{i=0}^{L} S_i + \frac{k-1}{N-LK-1} S_N \\ \varphi_{LK+k} = \sum_{i=0}^{L} \Phi_i + \frac{k-1}{N-LK-1} \Phi_N \end{cases}, S_0 \stackrel{def}{=} 0, \Phi_0 \stackrel{def}{=} 0,$$

wherein, $S_i$ denotes the translation vector between an ith pair of adjacent infrared images in the second infrared image sequence, $\varphi_i$ denotes the rotation angle between the ith pair of adjacent infrared images in the second infrared image sequence.

12. The image information generation method according to claim 9, wherein K is ½ to ¼ of a frame rate of sampling of the first infrared image sequence.

13. The image information generation method according to claim 6, wherein the step of correcting respective infrared images in the first infrared image sequence comprises: cutting out a part of the translated and rotated infrared image beyond a view range of the reference image, to obtain a corresponding corrected infrared image.

14. The image information generation method according to claim 13, wherein the step of removing at least the vein regions from respective infrared images in the corrected first infrared image sequence to obtain image information of remaining regions as image information for pulse wave measurement further comprises: determining a region of missing image information in the view range of the reference image in the corrected first infrared image, and removing the region of the missing image information and the vein regions, to obtain the remaining region.

15. The image information generation method according to claim 2, wherein the method further comprises: performing image analysis on vein patterns recognized in at least one infrared image in the second infrared image sequence, to obtain pattern features for use in identity recognition.

16. A pulse wave measurement system comprising:
   a near-infrared light source, configured to irradiate a target part with infrared light;
   an infrared image acquisition device, configured to acquire an infrared image sequence of the target part, each infrared image in the infrared image sequence including at least a vein pattern; and
   a pulse wave measurement device, connected with the infrared image acquisition device communicatively, and including a processor, a memory and instructions stored thereon,
   wherein when the processor executes the instructions, the processor implements an image information generation method comprising:
      with respect to a target part, acquiring a first infrared image sequence, each infrared image in the first infrared image sequence including at least the vein pattern,
      by registering the vein pattern in each infrared image in the first infrared image sequence, correcting each infrared image in the first infrared image sequence, thereby obtaining a corrected first infrared image sequence, and
      removing at least vein regions from respective infrared images in the corrected first infrared image sequence, to obtain image information of remaining regions as image information for pulse wave measurement and
      uses image information of remaining regions obtained by the image information generation method to perform the pulse wave measurement.

17. The pulse wave measurement system according to claim 16, wherein a wavelength of the infrared light irradiated by the near-infrared light source is 740 nm-780 nm.

18. The pulse wave measurement system according to claim 16, wherein the step of, by registering the vein pattern in each infrared image in the first infrared image sequence, correcting each infrared image in the first infrared image sequence, thereby obtaining the corrected first infrared image sequence, further comprises:
   selecting a reference image and a second infrared image sequence in the first infrared image sequence;
   recognizing vein patterns in respective infrared images in the second infrared image sequence;
   determining motions between vein patterns recognized in respective infrared images in the second infrared image sequence;
   based on the determined motions between vein patterns, correcting respective infrared images in the first infrared image sequence, to eliminate motions of respective infrared images relative to the reference image.

19. An electronic device comprising:
   a processor; and
   a memory storing instructions, which when executed by the processor, cause the image processing device to perform the an image information generation method comprising:
   with respect to a target part, acquiring a first infrared image sequence, each infrared image in the first infrared image sequence including at least a vein pattern;
   by registering the vein pattern in each infrared image in the first infrared image sequence, correcting each infrared image in the first infrared image sequence, thereby obtaining the corrected first infrared image sequence; and
   removing at least the vein regions from respective infrared images in the corrected first infrared image sequence, to obtain image information of remaining regions as image information for pulse wave measurement.

20. The electronic device according to claim 19, wherein the wherein the step of, by registering the vein pattern in each infrared image in the first infrared image sequence, correcting each infrared image in the first infrared image sequence, thereby obtaining the corrected first infrared image sequence, further comprises:
   selecting a reference image and a second infrared image sequence in the first infrared image sequence;
   recognizing vein patterns in respective infrared images in the second infrared image sequence;
   determining motions between vein patterns recognized in respective infrared images in the second infrared image sequence; and
   based on the determined motions between vein patterns, correcting respective infrared images in the first infrared image sequence, to eliminate motions of respective infrared images relative to the reference image.

* * * * *